(12) United States Patent
Sproat

(10) Patent No.: US 6,230,354 B1
(45) Date of Patent: May 15, 2001

(54) ELECTRIC TOOTHBRUSH

(75) Inventor: Gustave Sproat, Paris la Defense Cedex (FR)

(73) Assignee: Moulinex S.A., Cormelles le Royal (FR)

( * ) Notice: Subject to any disclaimer, the term of this patent is extended or adjusted under 35 U.S.C. 154(b) by 0 days.

(21) Appl. No.: 09/201,152

(22) Filed: Nov. 30, 1998

(51) Int. Cl.$^7$ .............................. A61C 17/26; A46B 13/02
(52) U.S. Cl. ......................... 15/28; 15/167.1; 15/DIG. 5
(58) Field of Search .................................. 15/28, DIG. 5, 15/167.1, 22.1

(56) References Cited

U.S. PATENT DOCUMENTS

| | | | |
|---|---|---|---|
| 5,467,495 | * 11/1995 | Boland et al. ............................ | 15/28 |
| 5,652,990 | * 8/1997 | Driesen et al. ........................... | 15/28 |
| 5,953,783 | * 9/1999 | Hahn ................... | 15/167.1 |
| 6,021,538 | * 2/2000 | Kressner et al. .......................... | 15/28 |

FOREIGN PATENT DOCUMENTS

2587183 * 3/1987 (FR) .

* cited by examiner

*Primary Examiner*—Robert J. Warden, Sr.
*Assistant Examiner*—Kaj K. Olsen
(74) *Attorney, Agent, or Firm*—Young & Thompson

(57) ABSTRACT

In an electric toothbrush having a body forming a handle containing a drive, an arm and a head which extend in prolongation of that arm and which are provided with a brush including a circular plate of clumps of bristles and which is driven in rotation about an orthogonal axis by a motion transmission device coupled to a motor shaft driven by the drive, the circular plate has a central region having a first predetermined number of clumps of bristles whose free ends are located in a same plane $P_1$, a peripheral region 16 having a second predetermined number of clumps of bristles whose free ends 18 are located within the plane $P_1$ and a plane $P_2$ located below the plane $P_1$, as well as an intermediate region with a third predetermined number of clumps of bristles whose free ends are located in the plane $P_2$.

8 Claims, 3 Drawing Sheets

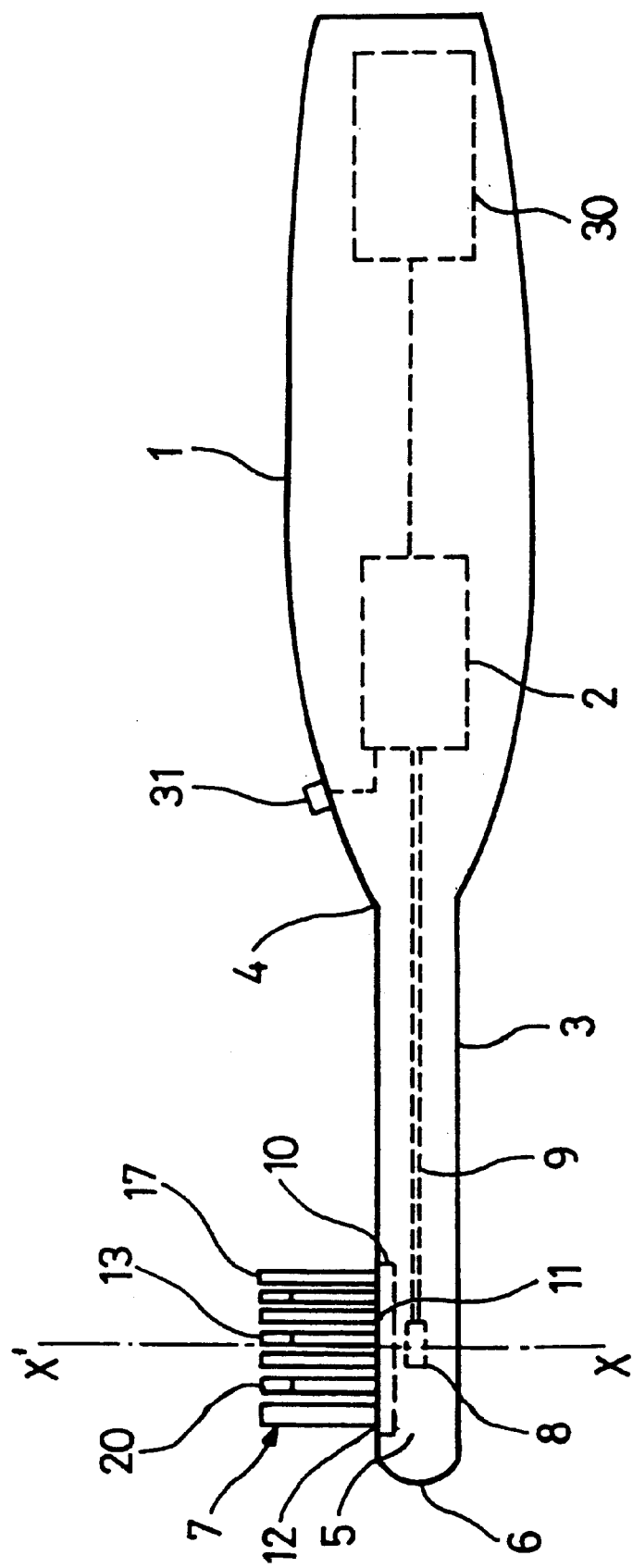

FIG_2
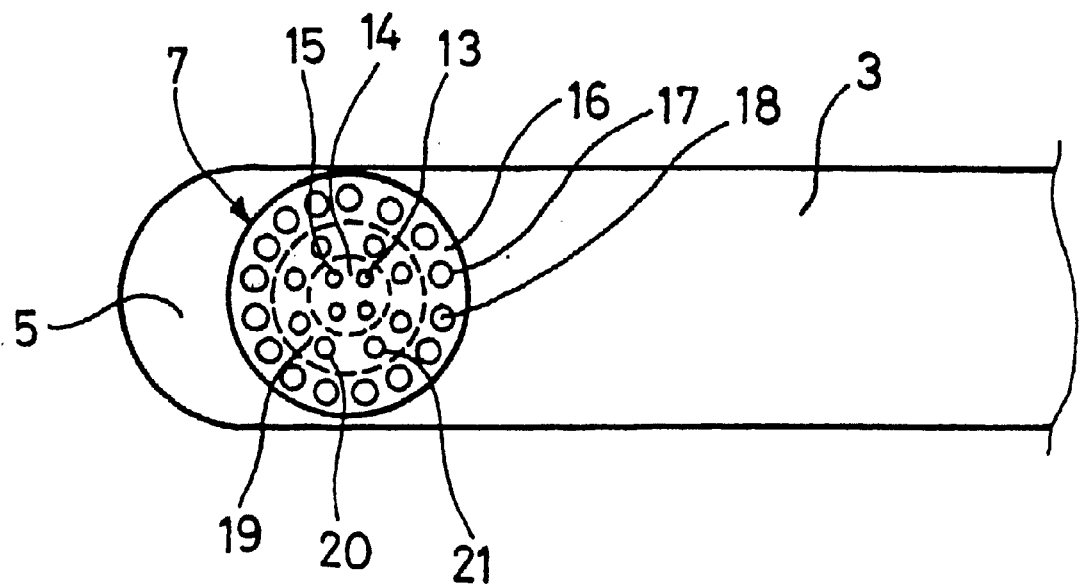
FIG_3
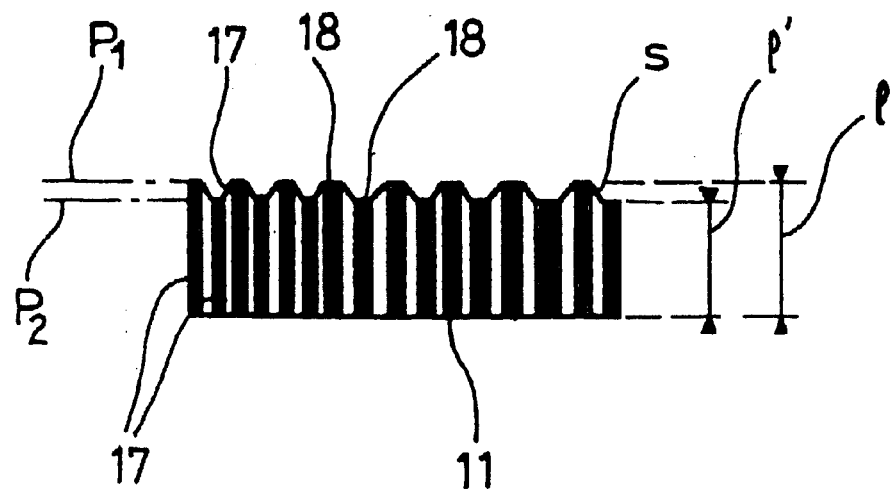

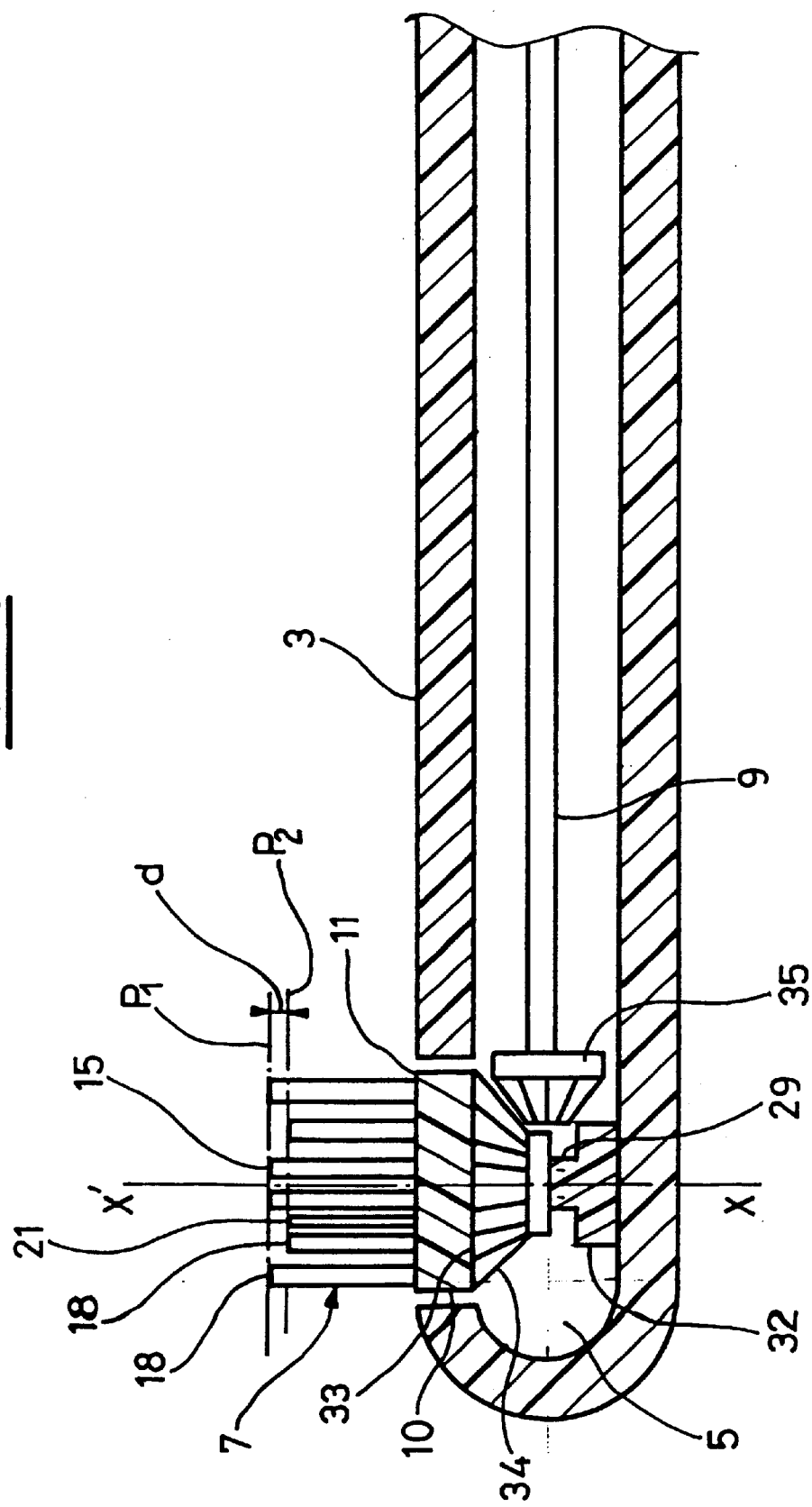

ELECTRIC TOOTHBRUSH

CROSS REFERENCES TO RELATED APPLICATIONS

This application corresponds to French application 97/12383 of Oct. 3, 1997, the disclosure of which is incorporated herein by reference.

BACKGROUND OF THE INVENTION

The present invention relates to an electric toothbrush comprising a body forming a handle and containing therein drive means, an arm whose first end is connected to said body and a head which extends in prolongation of said arm from the side of its second end and which is provided with a brush adapted to be driven in rotation about an axis X—X' by a movement transmission device coupled to a motor shaft driven by the drive means, said brush comprising a circular plate whose external surface is provided with holes in which are inserted clumps of bristles parallel to each other and mounted perpendicular to the external surface.

DESCRIPTION OF THE RELATED ART

For dental hygiene, brushing the teeth is fundamental and it is indispensable for an individual to clean his teeth by carrying out energetic brushing of all the surfaces of the teeth in the jaw.

Generally speaking, in electrical toothbrushes of known type, the brushes are provided with clumps of bristles whose operative ends coming into contact with the teeth are located in a same plane. Thus, during brushing the teeth from the rear of the jaw which have a relief in the form of a depression at their summit, the clumps of bristles of the brush do not totally match the shape of the teeth and hence do not perform optical brushing of the recess. Moreover, during brushing the inter-dental spaces with clumps of bristles located at the periphery of the circular plate, said clumps of bristles slide over said inter-dental spaces and do not effectively dislodge food particles that are caught and held strongly in said spaces.

SUMMARY OF THE INVENTION

The object of the invention is to overcome the mentioned drawbacks by providing a new brush for an electric toothbrush whose clumps of bristles have optimum efficiency without increasing the complexity of production of such a brush.

According to the invention, the circular plate comprises a central zone having a first predetermined number of clumps of bristles whose free ends are located in a same plane $P_1$, a peripheral region comprising a second predetermined number of clumps of bristles whose free ends are located alternately either in plane $P_1$, or in a plane $P_2$ located below the plane $P_1$ as well as an intermediate region comprising a third predetermined number of clumps of bristles whose free ends are located in the plane $P_2$.

Thanks to this particular implantation of the clumps of bristles of the brush as well as the difference in level between the different free ends of the clumps of bristles, the brushing of the teeth is substantially improved. Thus, the brush according to the invention comprises clumps of bristles in the central region whose ends are higher than the free ends of the clumps of bristles in the intermediate region and, because of this, for teeth having a contour in the form of a recess at their summit, the free ends of the clumps of bristles match perfectly said contours thereby permitting good brushing of all the surfaces of the teeth. Moreover, the alternation according to two planes of the free ends of the clumps of bristles implanted in the peripheral region of the circular plate, gives rise to a whipping motion of the clumps of bristles in the dental interstices. This whipping movement is due to a variation of the density of the clumps of bristles at these locations and thus facilitates effective brushing of the dental interstices which are often difficult to clean.

BRIEF DESCRIPTION OF THE DRAWINGS

The characteristics and advantages of the invention will become apparent from the description which follows, given by way of non-limiting example, with reference to the accompanying drawings, in which:

FIG. 1 is a schematic elevational and side view of an electric toothbrush according to the invention;

FIG. 2 shows a fragmentary schematic view from above and on a larger scale, of the head of the electric toothbrush of FIG. 1, and whose brush comprises a central region, an intermediate region and a peripheral region;

FIG. 3 is a developed view of the arrangement of the clumps of bristles of the peripheral region of the brush; and FIG. 4 is a fragmentary vertical cross-sectional schematic view, on a larger scale, of the head of the electric toothbrush of FIG. 1.

DESCRIPTION OF THE PREFERRED EMBODIMENTS

As shown in FIG. 1, an electric toothbrush comprises a body 1 forming a handle and containing within it drive means 2 shown in broken lines, an arm 3 whose first end 4 is connected to said body 1 and a head 5 which extends in prolongation of said arm from the side of its second end 6 and which is provided with a brush 7 adapted to be driven in rotation about an orthogonal axis X—X' by a movement transmission device 8 shown in broken lines, connected to a motor shaft 9 shown in broken lines and driven in rotation by the drive means. The drive means transmit to the brush 7 an alternating or continuous rotation in a same direction. Said brush 7 comprises a circular plate 10 whose external surface is provided with holes 12 in which are inserted clumps of bristles 13, 17 and 20 that are parallel to each other and are mounted perpendicularly relative to the external surface 11. The bristles forming the clumps of bristles 13, 17 and 20 are for example flexible filaments of synthetic fiber, for example nylon (trademark) or flexible filaments of natural silk.

The body 1 of such an electric toothbrush is generally adapted to be received, when not in use, in a suitable recess which provides a support (not shown), said support being provided with an electric supply cord adapted to be connected to a current source, namely an AC supply.

The drive means 2 are constituted for example by a DC motor adapted to be supplied by a rechargeable battery 30 of known type and shown in broken lines. Said battery is automatically charged when the body of the electric toothbrush is placed in the recess of the support and when the cord of said support is connected to the electrical supply.

A control switch 31 is mounted on the handle, in front of the latter, to control the operation of the motor 2. When the control switch 31 is closed, the motor 2 drives the motor shaft 9 which also causes the brush 7 to turn by means of the movement transmission device 8.

In the example shown in FIG. 4, the brush 7 is mounted on a pivot 29 having the same axis as the axis X—X', disposed above and secured to a base 32 mounted within the head 5 of the brush 7. The base 32 and the pivot 29 can be of a single piece entirely cast in synthetic material or the like. The brush 7 whose external surface 11 receives the clumps of bristles is flat, comprises an internal surface 33 carrying a conical return pinion 34 in engagement with a drive pinion 35 secured to the motor shaft 9. Thus, the conical return pinion 34 and the drive pinion 35 constitute the device 8 for transmission of the rotation of the motor 2 to the circular plate 10.

According to the invention, and as shown in FIGS. 2 and 4, the circular plate 10 comprises a central region 14 shown in broken lines and comprising a first predetermined number of clumps of bristles 13 whose free ends 15 are located in a same plane $P_1$, a peripheral region 16 shown by broken lines and comprising a second predetermined number of clumps of bristles 17 whose free ends 18 are located alternately either in the plane $P_1$, or in a plane $P_2$ positioned below the plane $P_1$, as well as an intermediate zone 19 shown by broken lines and comprising a third predetermined number of clumps of bristles 20 whose free ends 21 are located in the plane $P_2$.

The plane $P_1$ being located at a distance $d$ from the plane $P_2$, the distance $d$ has a value substantially equal to 1.5 mm. The distance $d$ has been carefully selected such that the free ends 15 and 21 of the clumps of bristles 13 and 20 of the central region 14 and of the intermediate region 19, match the shape of the teeth of the jaw, particularly the teeth having a contour in the form of a recess at their summit. Thus, the free ends 15, 18 and 21 of the clumps of bristles 13, 17 and 20 of the brush 7 are in contact with all of the contours of the teeth of the jaw.

The peripheral region 16 of the circular plate 10 comprises at least one row of clumps of bristles 17 forming an external crown whose free ends 18 of the clumps of bristles 17 are arranged on a sinusoid $S$ as is shown in FIG. 3. The intermediate region 19 of the circular plate 10 comprises at least one row of clumps of bristles 20 forming an intermediate crown. In the embodiment shown in FIG. 2, the peripheral region 16 has sixteen clumps of bristles 17, the intermediate zone 19 has eight clumps of bristles 20 and the central region 14 has four clumps of bristles 13. This implantation of the clumps of bristles 13, 17 and 20 into the brush 7 considerably increases the efficiency of brushing the teeth.

Said clumps of bristles 13, 17 and 20 implanted on the flat external surface of the circular plate 10, have different lengths. These clumps of bristles of the central region 14 have a length $l$ delimited between said flat external surface 11 and their free ends 15. The clumps of bristles 20 of the intermediate region 19 have a length $l'$ delimited between the flat external surface 11 and their free ends 21 and less than the length $l$. The clumps of bristles 17 of the peripheral region 16 have alternately the length $l$ and the length $l'$. Thus, when brushing the teeth, there is obtained an effect of alternate blows by flexure of the longest clumps of bristles 17.

In one embodiment, the length $l$ has a value substantially equal to 10 mm whilst the length $l'$ has a value substantially equal to 8.5 mm.

Thus, the clumps of bristles 17 of the crown 16 alternate in length by about 1.5 mm to ensure good cleaning of the dental interstices whilst the clumps of bristles 13 of the central region 14 have a length greater than the length of the clumps of bristles 20 and the intermediate crown 19, so as to match as well as possible the shape of the teeth and to perform more effective brushing.

The operation of the electric toothbrush according to the present invention is extremely simple and will be described hereinafter with reference to FIGS. 1, 2 and 4. The user having gripped the handle of the electric toothbrush, closes the control switch 31 to start the motor 2. In the course of rotation of the motor 2, the motor shaft 9 drives the drive pinion 35 which engages with the conical return pinion 34 to cause to turn also the circular plate 10. Upon rotation of the circular plate 10, the clumps of bristles 13, 11 and 20 are driven in rotation and are ready to brush the teeth. Thus, during brushing a tooth located at the rear of the jaw and having a shape in the form of a recess at its summit, the free ends 18 of the clumps of bristles 17 of the peripheral region 16 have a whipping action into the dental interstices to sweep bits of food or food residue which became lodged, as well as the free ends 15 and 21 of the clumps of bristles 13 and 20 of the central region 14 and of the intermediate region 19, which respectively brush the hollow part and its periphery to remove any residues deposited therein and thereby preventing the formation of cavities.

What is claimed is:

1. In an electric toothbrush comprising a body (1) providing a handle and containing in the handle drive means (2), an arm (3) whose first end (4) is connected to said body (1) and a head (5) which extends in prolongation of said arm (3) from the side of the second end (6) of the arm (3) and which is provided with a brush (7) adapted to be driven in rotation about an orthogonal axis X—X' by movement transmission means (8) coupled to a motor shaft (9) driven by drive means (2), said brush (7) comprising a circular plate (10) whose external surface (11) is provided with holes (12) in which are inserted clumps of bristles (13, 17 and 20) parallel to each other and mounted perpendicularly relative to said external surface;

the improvement wherein:

the circular plate (10) comprises a central region (14) comprising a first predetermined number of clumps of bristles (13) whose free ends (15) are located in a same plane $P_1$, an intermediate region (19) about said central region and comprising a second predetermined number of clumps of bristles (20) whose free ends (21) are located in said plane $P_2$, and a peripheral region (16) about said intermediate region and comprising a third predetermined number of clumps of bristles (17) whose free ends (18) are located in the plane $P_1$, in a plane $P_2$ wherein said orthogonal axis being orthogonal to said circular plate and said bristles whose free ends are located in plane $P_1$ have a first length greater than those bristles whose free ends are located in plane $P_2$ and have a second length; and wherein said peripheral region (16) comprises at least one row of clumps of bristles (17) forming an external crown and whose free ends (18) define a virtual line having a sinusoidal shape with the upper and lower bounds of the sinusoidal shape are $P_1$ and $P_2$ respectively.

2. An electric toothbrush according to claim 1, wherein the intermediate region (19) comprises at least one row of clumps of bristles (20) forming an intermediate crown (19).

3. An electric toothbrush according to claim 2, wherein said peripheral region (16) has sixteen clumps of bristles (17), said intermediate region (19) has eight clumps of bristles (20) and said central region (14) has four clumps of bristles (13).

4. An electric toothbrush according to claim 1, wherein said plane $P_1$ is located at a distance $\underline{d}$ from said plane $P_2$, the distance $\underline{d}$ having a value substantially equal to 1.5 mm.

5. An electric toothbrush according to claim 1, wherein said external surface (11) of the circulate plate (10) is flat, the clumps of bristles (13) of the central region (14) have the first length delimited between said flat external surface (11) and their free ends (15), the clumps of bristles (20) of the intermediate region (19) have the second length delimited between said flat external surface (11) and their free ends (21), and the clumps of bristles (17) of the peripheral region (16) have lengths varying from the first length to the second length.

6. An electric toothbrush according to claim 5, wherein said first length has a value substantially equal to 10 mm, and said second length has a value substantially equal to 8.5 mm.

7. An electric toothbrush according to claim 1, wherein said bristles forming said clumps of bristles (13, 17 and 20) are flexible filaments of natural silk.

8. An electric toothbrush according to claim 1, wherein the bristles forming said clumps of bristles (13, 17 and 20) are flexible filaments of synthetic fiber.

\* \* \* \* \*